United States Patent [19]

Wareing

[11] Patent Number: 4,474,971

[45] Date of Patent: Oct. 2, 1984

[54] (TETRAHYDROPYRAN-2-YL)-ALDEHYDES

[75] Inventor: James R. Wareing, Randolph, N.J.

[73] Assignee: Sandoz, Inc., E. Hanover, N.J.

[21] Appl. No.: 427,605

[22] Filed: Sep. 29, 1982

[51] Int. Cl.$^3$ ............................................ C07D 309/06
[52] U.S. Cl. .................................... 549/214; 549/417; 549/415; 549/396; 549/206
[58] Field of Search ........................ 549/417, 214, 415

[56] References Cited

PUBLICATIONS

Yang et al., Tetrahedron Letters, 23, 4305(1982).

Primary Examiner—Nicky Chan
Attorney, Agent, or Firm—Gerald D. Sharkin; Richard E. Vila; Frederick H. Weinfeldt

[57] ABSTRACT

Single enanitiomers of 6-(2-hydrocarbyl-substituted ethenyl)-bearing, 4-hydroxy tetrahydro-2H-pyran-2-ones, e.g., 6α-[2-(2-methyl-1-naphthyl)ethenyl]-3,4,5,6-tetrahydro-4β-hydroxy-2H-pyran-2-one (4R,6S) are obtained by a multi-step process which includes protecting and deprotecting hydroxy groups at various stages.

5 Claims, No Drawings

(TETRAHYDROPYRAN-2-YL)-ALDEHYDES

This invention relates to a process for the preparation of pyranone compounds and more particularly to a process for the preparation of a single enantiomer of 6-[2-(hydrocarbyl)ethenyl]-3,4,5,6-tetrahydro-4-hydroxy-2H-pyran-2-one derivatives, and to intermediates in said process, and to individual process steps.

The process of this invention yields tetrahydropyran-2-one forms of the 3,5-dihydroxypentanoic acid esters disclosed in European Pat. No. 11,928 (published June 11, 1980; available as Derwent No. 41,925 C). The tetrahydropyranones disclosed in European Pat. No. 24,348 (Derwent No. 17673 D); corresponding to U.S. Application Ser. No. 67,574 (filed Aug. 17, 1979), may likewise be obtained by the process of this invention as well as those of European Pat. No. 10,951 (Derwent No. 36,970 C). Such compounds are useful in the treatment of diseases or conditions such as atherosclerosis, as they are inhibitors of the biosynthesis of cholesterol, in the manner of compactin or analogs thereof such as are disclosed in U.S. Pat. No. 4,282,155 (issued Aug. 9, 1981).

The process of this invention provides the 2H—pyran-2-one derivatives exclusively in the 4R,6S configuration of the naturally occuring compounds (i.e., compactin) with none of the undesired stereochemical or optical isomers being produced.

The final compounds of the process of this invention may conveniently be represented by the formula I:

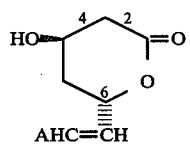

in which A is an aryl or partially reduced aryl hydrocarbyl radical of the formula:

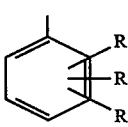 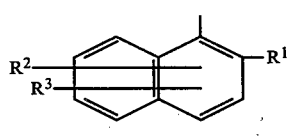

(a)  (b)

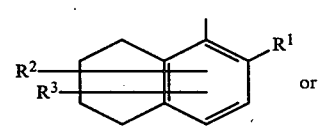

or (c)

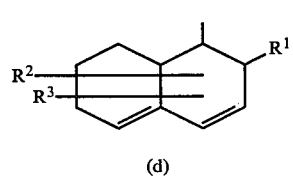

(d)

in which $R^1$, $R^2$ and $R^3$ are independently, halo having an atomic weight of from about 19 to 35, i.e. For Cl, hydrogen, or lower alkyl having from 1 to 4 carbon atoms. It is preferred that for radical (a) at least one of $R^1$ and $R^2$ is halo, and for radicals (b), (c) and (d) that $R^1$ is methyl.

The last steps of the process of this invention are conveniently represented in Reaction Scheme A, below, wherein A is as defined above, Ph is phenyl, halo⊖ is a halide ion, i.e., iodide, bromide or chloride, and $P^1$ and $P^2$ are protective groups which may be the same or different; preferably they are different.

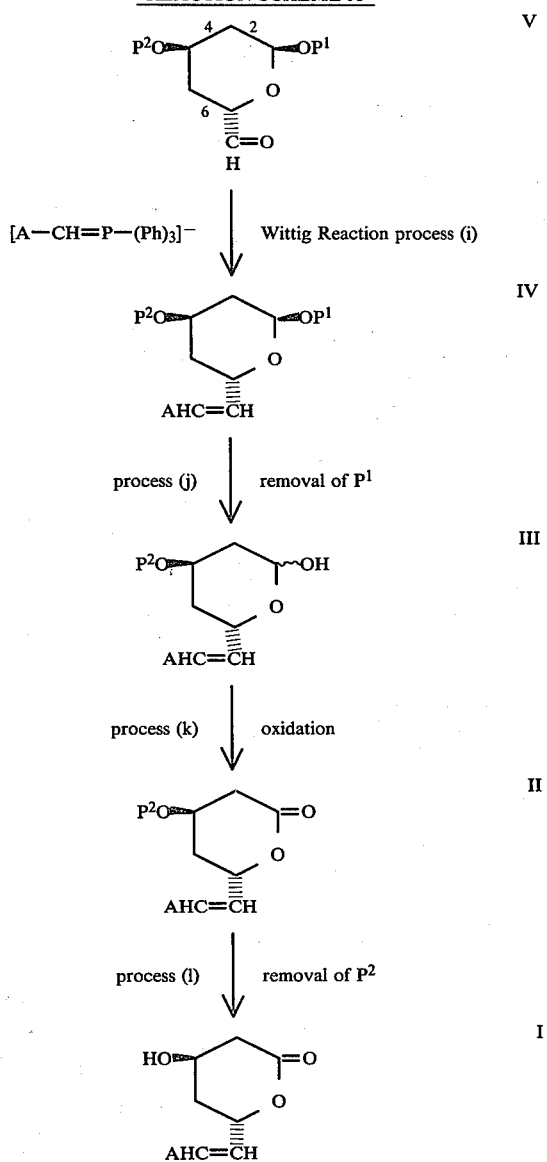

Compounds V depicted in Reaction Scheme A, above are obtainable by a series of proven steps starting with an oxirane compound (A) as represented in Reaction Scheme B, below, in which, by way of illustration, a particular compound V is formed, i.e. V', in which $P^2$ (as the 4β-position) is diphenyl t-butylsilyl* and $P^1$ (at the 2β-position) is methyl. At the 6α-position, protection is temporarily provided ($P^3$) in the reaction scheme by the trityl radical, i.e., triphenylmethyl, to protect the hydroxymethyl function while $P^2$ is introduced, during process f) and then removed (process g), so that it can be oxidized to an aldehyde function.

*t-bu=t-butyl in Reaction Scheme A

Preferred Compounds V are those in which P¹ is unbranched alkyl having from 1 to 4 carbon atoms, especially methyl; and P² is preferably a tri-substituted silyl**, e.g., diphenyl t-butyl silyl; tri-isopropylsilyl or dimethyl t-butyl silyl; especially, diphenyl t-butylsilyl. Accordingly, these preferences likewise apply to products IV, III and II obtained therefrom, as shown in Reaction Scheme A.

**of formula (t) defined below

REACTION SCHEME B

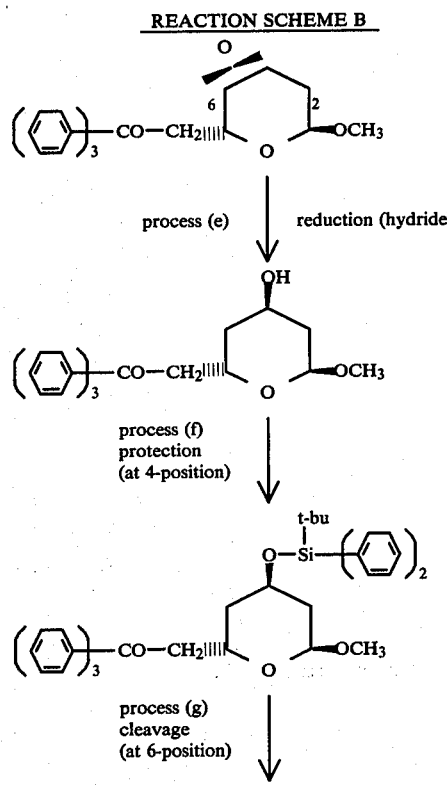

REACTION SCHEME B -continued

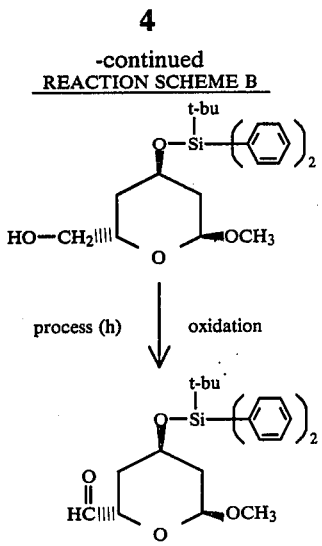

The method of obtaining starting materials for preparing compounds V of Reaction Scheme B is illustrated in Reaction Scheme C, below, in which by way of illustration the particular protecting groups are respectively methyl as P¹, diphenyl-t-butylsilyl as P² and trityl as P³, as in Reaction Scheme B, above.

Compounds A of Reaction Scheme C are obtainable by employing glucose as starting material, by adapting the method of Corey, J. Am. Chem. Soc. 102 (4) 1439 (1980) and are represented in Reaction Scheme C, below, in which Ac is acetyl, ipr is isopropyl and Ph is phenyl, by way of illustration.

It is understood that in process a), the methanol used therein represents P¹OH, and the preferences disclosed above apply. Hence where P¹=P¹', i.e., unbranched alkyl of 1 to 4 carbon atoms, the product (X) obtained therefrom will accordingly bear the group 2β-OP¹. Likewise subsequent products thereof, Y, Z, A to D, V and IV will likewise bear whatever group is introduced onto compound X as P¹ at the 2β-position, as a result of the choice of alcohol in process (a).

REACTION SCHEME C

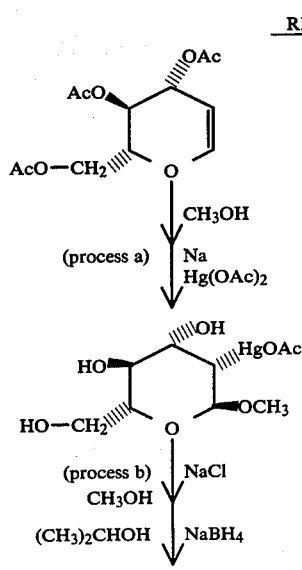

-continued
REACTION SCHEME C

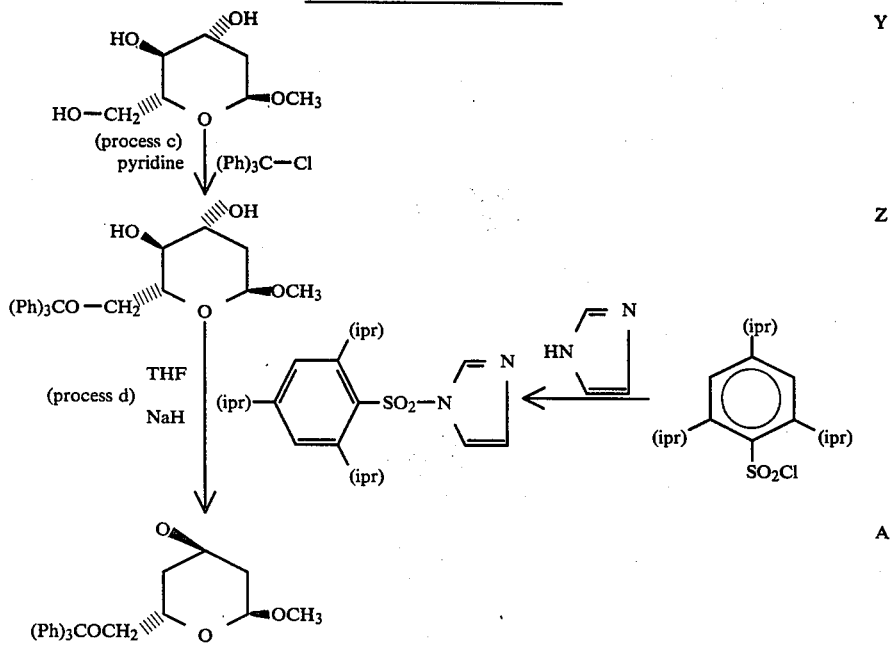

It will be appreciated that on compounds A and B, hydroxy functions at both the 2-position and the 6α-position, are protected. The protecting group at the 6α-position is removed (in process b) to expose the hydroxymethyl radical, and later the protecting group at the 2-position is removed (process g) to expose the 2-hydroxy substituent. In process (l) the "last" protecting group (P²) is removed to yield the desired compound I.

Protecting agents suitable for use in this invention are generally known, e.g., independently, n-alkyl having from 1 to 6 carbon atoms; benzyl; triphenylmethyl; tetrahydrofuran-2-yl; tetrahydropyran-2-yl; 4-methoxytetrahydropyran-4-yl; tri-substituted silyl; formyl, an n-alkonoyloxy the alkyl portion having from one to 6 carbon atoms. Those protective groups employed in the Reaction Schemes, above, being particularly preferred. It will be noted that the protecting groups P¹; P² and P³ are introduced and removed (deprotected) at various stages in the overall process, i.e., no more than one at a time. Hence, all three protecting groups P¹, P² and P³ are preferably different, so that by choice of particular groups to be employed and selection of reaction conditions, deprotection at a desired position can be achieved, while retaining any other protecting groups as desired. Indeed, intermediates C is shown in Reaction Scheme B to bear 3 protecting groups. Tri-substituted silyl groups include those of the structure:

$$-\underset{\underset{R^c}{|}}{\overset{\overset{R^a}{|}}{Si}}-R^b \qquad (t)$$

in which each of $R^a$, $R^b$ and $R^c$ is, independently alkyl having from 1 to 6 carbon atoms or phenyl, provided that not more than 2 or $R^a$, $R^b$ and $R^c$ are phenyl.

In carrying out the processes of this invention, it is preferred that P¹ be P¹' which is unbranched alkyl having from 1 to 4 carbon atoms, e.g., methyl, and the P² be P²' which is tri-substituted silyl, e.g., tri-isopropyl silyl, diphenyl t-butyl silyl; dimethyl t-butylsilyl.

It will be appreciated that throughout this disclosure compound structures are depicted in "flat" (two dimensional) form. However, the compounds I (and intermediates) are three dimensional and may alternatively be represented, e.g., by the formula:

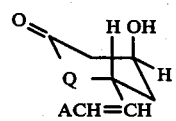

in which A is as defined above. The hydrogen atom and hydroxy function at the 4-position and the hydrogen atom and ethenyl unit at the 6-position exist in a specific relationship with the tetrahydro-pyran-2-one nucleus and each other in the final product and various intermediates. Various chemical processes may provide compounds bearing hydroxy and/or ethenyl units at the 4- and 6-position respectively, but not necessarily in the desired configurational relations in very high proportions, in mixtures that are difficult and inefficient to separate in order to recover the desired isomers. Of course, the more sites on the molecule having variable configuration, the more difficult becomes the method of preparation and recovery of a product of desired configuration, i.e., the 6-S, 4-R isomer.

The process of this invention provides numerous advantages for the preparation of the compounds of formula I. For example, it provides the desired final product in relatively high proportion and having the relative steric relationship on the tetrahydropyran-2-one portion established (4-R, 6-S) thus minimizing the cost and effort of recovering such isomers from mixtures of close isomers which are difficult and tedious to resolve, as are obtained by other processes.

Embodiments of this invention are novel intermediates of formulas II, III, IV and V as described above (depicted in Reaction Scheme A), and methods of preparing them.

Process l) comprises deprotecting a compound II to obtain the corresponding 4β-hydroxy bearing compound, i.e., a compound I. The deprotection step may be carried out by methods that are well known to the art as conventional for the removal of a group protecting (or masking) a hydroxy function. Where $P^2$ is diphenyl t-butylsilyl* a fluoride reagent is conveniently employed in the deprotection thereof as is well known in the art, e.g., in a suitable inert medium, e.g., a cyclic ether, such as tetrahydrofuran (THF), at moderate temperature, e.g., from about 20° to 60° C., preferably at room temperature (20°–30° C.), employing tetra-n-butyl ammonium fluoride in the presence of glacial acetic acid (preferably in slight molar excess, e.g., of about 1.2 to 1.8 mol of acetic acid per mol of the fluoride).
*or other tri-substituted silyl as disclosed above.

Process k) which involves oxidizing a compound III (at the 2-position) to its corresponding 2-ketone (II) may be accomplished by methods that are well-known in the art. For example, a compound III may be treated with pyridinium chlorochromate (PCC) in an inert medium, e.g., a chlorinated hydrocarbon, such as methylene chloride, at moderate temperatures, e.g., at from about 10° to 80° C., preferably at from 20°–30° C.; the $P^2$ used, being stable under such reaction conditions. The $P^2$ used being stable under such reaction conditions.

In process j) $P^1$ (at the 2-position) is removed to convert a compound IV to its corresponding alcohol (III). Where $P^1$ is a lower alkyl group, it is conveniently cleaved by treatment with an aqueous acid such as dilute hydrochloric acid, e.g., 10%, in an inert medium, e.g., a cyclic ether such as tetrahydrofuran, at moderate temperatures, e.g., +10° to 100° C., conveniently, e.g., at 20° to 30° C.

In process (i), the hydrocarbyl substituted-ethenyl unit is introduced, by a Wittig reaction involving treating the aldehyde function of a compound V with an A-bearing reagent derived from an A-substituted-methyl-triphenyl-phosphonium halide; the halide being, iodo, bromo or chloro, under essentially anhydrous conditions at moderate temperature, e.g., from about −10° to 80° C., (preferably initially at temperatures of from about −10° to 0° C., e.g., −5°), in an inert medium such as hydrocarbon, e.g., benzene or toluene, or a cyclic ether, e.g., THF. The reagent* is prepared by treating an A-substituted-methyl, triphenyl phosphonium halide with a strong base, e.g., an alkali metal hydrocarbon, such as butyl lithium, in an inert medium, e.g., a hydrocarbon, such as benzene or toluene, or a cyclic ether, e.g., THF, at reduced temperatures, e.g., −10° to 0° C., e.g., at −5°, under anhydrous conditions, and using the resulting reagent in situ.
*the reagent is an A-substituted methylidene triphenyl phosphorane of the formula: A-CH=P-(phenyl)$_3$ In process h), the hydroxymethyl radical is oxidized to an aldehyde function. The oxidation may be carried out by conventional means. A convenient method of carrying out the oxidation is by the Swern procedure, i.e., by treating a compound with the reagent formed by oxalyl chloride, dimethyl sulfoxide and triethylamine at reduced temperatures, e.g., about −60° to −40° C., e.g., about −50°, in an inert medium e.g., a chlorinated hydrocarbon; such as methylene chloride, under essentially anhydrous conditions.

The final products and intermediate compounds described herein may be recovered and refined, where such is desired, by conventional means, such as by crystallization, distillation or chromatographic techniques such as column or thin layer chromatography.

Reagents and reactants described herein, e.g., compounds A, and W to Z, (or analogs thereof) are known and obtainable by known means, or where not known, may be obtained by adaptation of methods reported in the literature for the preparation of known analogs; many such materials being commercially available.

UTILITY STATEMENT

The compounds of formula (I) are useful because they possess pharmacological activity in animals. In particular, the compounds are useful as hypocholesterolemic agents as indicated by the inhibition of 3-hydroxy-3-methylglutaryl-COA (HMG-COA) reductase activity in rat liver microsomes. The liver microsome suspensions are freshly prepared from Sprague-Dawley rat livers in buffer A containing 0.1 mole sucrose, 0.05 moles potassium chloride, 0.04 mole potassium phosphate, 0.03 moles EDTA and 10 millimoles DTE at pH 7.2 essentially in accordance with the procedure of Hiller and Gould (Biochem. Biophys. Res. Commun. 50, 859–865, 1973; J. Biol. Chem., 249, 5254–5260, 1973). The HMG-COA reductase activity inhibition was determined by incubating 200 microliter aliquots of microsomal suspension containing 150 to 200 milligrams of microsomes per milliliter with 10 milliliters aliquots containing 0.00095, 0.0095, 0.095, 0.952 and 9.52 millimoles of compound of formula I in accordance with the procedure of C.D. Pormanen, et al; J. Biol. Chem., 252, 1561–1565 (1977). The HMA-COA reductase activity was measured in accordance with the procedure of M. E. Ackermann, et al; J. Lipid Research, 18, 408–413 (1977).

For the above use the compounds of formula (I) may be combined with pharmaceutically acceptable carriers or adjuvants and may be administered orally or parenterally. They may be administered in such forms as tablets, dispersible powders, granules, capsules, syrups and elixirs and parenterally as non-aqueous solutions, suspensions, dispersions, emulsions and the like, e.g., a sterile injectable non-aqueous solution.

The HMG-COA reductase inhibiting effective amount of the compounds of formula (I) used in inhibiting or regulating biosynthesis of cholesterol will vary depending on the particular compound employed, the mode of administration, and the severity of the condition treated. However, in general, satisfactory results are obtained when the compounds are administered at a daily dosage of from about 1 milligram to about 666 milligrams per kilogram of animal body weight, typically given in divided doses two to four times per day. For most large mammals, the total daily dose is from about 10 to about 500 milligrams, and dosage forms suitable for internal administration comprise from about 2.5 to about 250 milligrams of the compounds in admixture with a solid or liquid pharmaceutical carrier or diluent.

Tablets and capsules containing the ingredients indicated below may be prepared by conventional techniques and are useful in treating hypercholesteremia at a dose of one tablet or capsule 2 to 4 times a day.

| Ingredient | Weight tablet | capsule |
| --- | --- | --- |
| 6α-[2-(2-methyl-1-naphthyl)-ethenyl] 3,4,5,6-tetrahydro-4β-hydroxy-2H—pyran-2-one, (4R, 6S) the product of Example 1, below. | 50 | 50 |
| tragacanth | 10 | — |
| lactose | 197.5 | 250 |
| corn starch | 25 | |
| talcum | 15 | |
| magnesium stearate | 2.5 | |
| Total | 300 mg. | 300 mg. |

In the following examples and preparations which are illustrative of the invention and the intermediates involved in their preparation, temperatures are in degrees in centigrade, and room temperature is 20° to 30° C., unless indicated otherwise. Where NMR characterization data is presented, the analysis is run in CDCl$_3$ and values given in ppm; digits in parenthesis are number of protons; and t=triplet, d=doublet, s=singlet, m=multiple and bs is broad singlet. J is coupling factor.

EXAMPLE 1

6α[2-(2-methyl-1-naphthyl)ethenyl]-tetrahydro-4β-hydroxy-2H-pyran-2-one (4R, 6S)

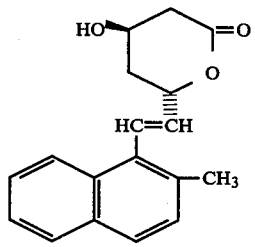

Step A, preparation of (acetato-o) tetrahydro-4α,5β-dihydroxy-6α-hydroxymethyl-2β-methoxy-2H-pyran-3-yl)-mercury* (a compound X)

*may also be called (4α,5β-dihydroxy 6α-hydroxymethyl-2β-methoxy-tetrahydro-2H-pyran-3-yl) mecuric acetate

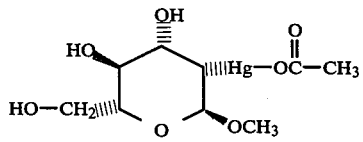

Under a nitrogen atmosphere, 300 mg of metallic sodium is dissolved in one liter of methanol (freshly distilled from magnesium) over about 10 minutes, with stirring. 136.1 g of tri-O-acetyl-D-glucal** is added (as a solid), which dissolves, and the mixture is cooled and stirred at room temperature, for one hour at which time TLC indicates methanolysis is complete. 159.35 g of mercuric acetate is slurried in one liter of freshly distilled methanol. The slurry is added to the reaction mixture through an addition funnel having a widebore stopcock, portionwise, over a period of one hour. As each portion is added, it dissolves in a short time. After the addition is completed stirring is continued (at room temperature and under nitrogen gas) for an additional four hours, at which time the reaction mixture is homogeneous and colorless. Heat is gently applied by a bath (not over 40°) to remove (under vacuum) 1,200 ml of solvent. The residue begins to solidify as it cools; and scratching the inside of the vessel over a period of about 30 minutes results in a granular solid product. The solids are collected on a sintered-glass filter, and the vessel rinsed with 50 ml. of ice-cold dry methanol, which is used to wash the filtered solids. The solids are washed with 300 ml of dry diethyl ether, and then dried (under vacuum) to obtain the title product of this step as a fine white powder. If desired a second crop may be obtained by adding enough methanol to the mother liquor to make it homogeneous, and then concentrating to a thick oil, which solidifies on standing, and on treatment as above, yields additional product as a white solid. The product of this step, is either used promptly for the next step, or held under nitrogen if not used promptly.

**may also be called 3β,4α-dihydroxy-2α-hydroxymethyl-2,3-dihydro-2H-pyranyl triacetate.

Step B, preparation of 4α,5β-dihydroxy-6α-hydroxymethyl-2β-methoxy-tetrahydro-2H-pyran (a compound Y)

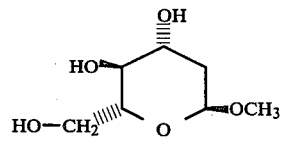

A slurry of 159.0 g of the product of step A above and one liter of methanol (freshly distilled from magnesium) is prepared. To the slurry is added 33.5 g of finely powdered solid sodium chloride. The mixture is stirred for about 5 minutes at room temperature resulting in a homogeneous solution, except for excess sodium chloride. The mixture is then cooled to 0° C. (with an external ice bath) and 10.7 g of sodium borohydride which had been finely powdered is slurried in one liter of dry isopropanol freshly distilled from BaO), is placed in an addition funnel having a wide-bore stopcock (Agitation is necessary to maintain the mixture in suspension). The slurry is added in small portions over 1.5 hrs. with ice-bath cooling in order to maintain internal temperature below 25°, as the reaction is exothermic and produces a gas and metallic mercury). When the addition is completed, the ice-bath is removed, and the suspension (gray) is allowed to stir for two hours. Solvent is vacuum distilled off (at below 40°) until the residue is almost dry, and one liter of ethyl acetate (freshly distilled from P$_2$O$_5$) is added. The slurry is cooled to about 0° and concentrated hydrochloric acid then added dropwise, with vigorous stirring. (The pH is checked after each 5 drops of the acid addition) until slightly acid, 50 g of solid sodium bicarbonate is immediately added; the entire acidification should be completed in less than 5 minutes. After stirring for about 5 minutes, 50 g of 4 A° molecular seive is added, and the reaction mixture filtered through a pad of celite supported on glass-wool in a sintered glass funnel, pre-wetted with dry ethyl acetate. The gray sludge in the funnel is washed 3 times with 100 ml portions of dry ethyl acetate and the combined ethyl acetate extracts evaporated to a thick colorless gum. The gum is dried under high vacuum for 1 hr. then held for about 18 hrs. in a vacuum oven in the presence of P$_2$O$_5$, and then placed under high vacuum for one hour which results in a waxy solid which upon standing (5 hours) becomes less waxy. The solids are triturated with dry diethyl ether to give solid title product of this step, m.p. 64°–66° (softening at 63°).

Step C, preparation of
4α,5β-dihydroxy-2β-methoxy-6α-triphenylmethoxymethyl-tetrahydro-2H-pyran (a compound Z)

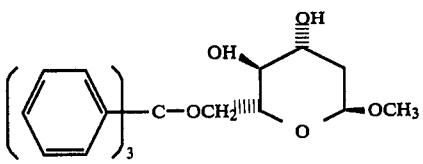

Under a nitrogen atmosphere 41.5 g of the triol product of Step B is mixed with one liter of pyridine (freshly distilled from potassium hydroxide) resulting in almost complete solution (as some solid remains in suspension, after ½ hr. stirring). 300 ml of dry dichloromethane is added with stirring, resulting in almost complete solution. 69.695 g of trityl chloride (solid) is added resulting in the solution turning slightly tan (without noticeable exotherm) and the mixture is stirred for about 18 hrs. under nitrogen during which a precipitate forms. The mixture is poured into 1.5 liters of ice-cold dilute hydrochloric acid (10%) and extracted 3 times with 200 ml portions of dichloromethane. The combined dichloromethane extracts are washed 6 times with 200 ml portions of ice-cold 10% hydrochloric acid, 2 times with 200 ml portions of saturated aqueous sodium bicarbonate, once with 200 ml of brine and then dried over anh. magnesium sulfate. The dried extracts are recovered by filtration and solvent removed under vacuum, to obtain a residue, which is a thick oil (partly solid, which smells of pyridine). The residue is redissolved in 500 ml of ethyl ether and 200 ml of dichloromethane, and the solution washed 5 times with 200 ml portions of ice-cold hydrochloric acid, twice with 200 ml portions of sat. aqueous sodium bicarbonate, once with brine, and dried over anhydrous magnesium sulfate. The dried solution (light yellow) is then evaporated under vacuum to obtain a tan foam, which is then dissolved in 200 ml of hot ethyl ether plus enough dichloromethane to make the mixture homogeneous. To the resulting solution is added pentane until cloudy; then allowed to stand at room temperature for about 48 hours, during which a precipitate forms. The solids are collected on a filter and washed with pentane to obtain the title product of this step, m.p. 140°–142°.

Step D, Preparation of
4β,5β-epoxy-2β-methoxy-6α-triphenylmethoxymethyl-tetrahydro-2H-pyran (a compound A)

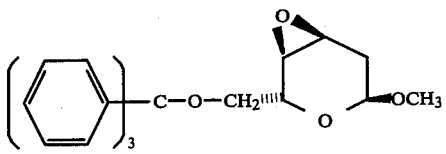

Under nitrogen, 9.6 g of sodium hydride (as a 50% dispersion in paraffin oil) is washed 3 times with 10 ml portions of pentane, 80 ml of hexamethylphosphoramide (HMPT) is added to the washed sodium hydride. 20.025 g of the diol product of Step C, dissolved in 100 ml of HMPT and the solution placed in an addition funnel, and cautiously added therefrom to the mixture at room temperature over a period of about 15 minutes (gas evolves). The addition funnel is rinsed with 20 ml of HMPT and the rinse added to the mixture, which is then stirred for 1.5 hrs. at room temperature, (bubbling stops and the reaction mixture is a light tan color). The reaction mixture is diluted with 100 ml of dry THF (freshly distilled) and the mixture cooled to −30° under N₂. 16.72 g of 2,4,6-triisopropylbenzenesulfonyl imidazol in 100 ml of dry THF is added drop-wise to the mixture over a period of about 1 hr. (−30° temperature being maintained). After addition stirring is continued for 3 hrs. at −30°. The reaction mixture is filtered (through filter paper containing celite, pre-wetted with THF), and the solids washed on the filter with 100 ml of THF. The filtrate is concentrated by vacuum-evaporated to obtain a viscous oil, which is poured into 2.5 liters of brine and extracted 5 times with 150 ml portions of diethyl ether. The combined ether extracts are washed twice with 50 ml of brine, dried over anh. magnesium sulfate and evaporated to a residue (thick oil). 10 to 15 ml of dichloromethane is added to the residue which is then warmed, and pentane added to give a volume of about 300 ml. Upon standing for about 18 hours a precipitate forms which is washed with pentane and recovered as a white solid. The solid is recrystallized from pentane-diethylether to yield the title product of this step m.p. 100°–102°. Additional product can be recovered from the mother liquor, if desired. The product of this step is also known as 3,7-dioxabicyclo-[4.1.0]heptane, 2-methoxy-4-triphenylmethoxy-2β,4α, 6β, 7β.

Step E, Preparation of
2β-methoxy-6α-triphenylmethoxymethyl-tetrahydro-2H-pyran-4β-ol (a compound B)

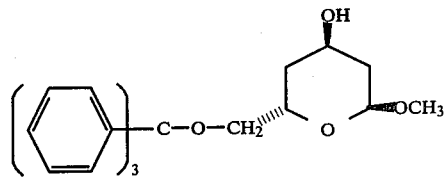

8.04 g. (20 mmole) of 4β,5β-epoxy 2β-methoxy-6α-triphenylmethoxymethyl-tetrahydro-2H-pyran is dissolved in 200 ml diethyl ether which is then cooled to 1° C. and 20 ml (20 mmole) of a 1 molar solution of lithium aluminum hydride in ether is added dropwise over five minutes maintaining the temperature at 1° C. After one hour at 1° C. and three hours at room temperature 20 ml of ethyl acetate is added slowly followed by 20 drops of H₂O. The reaction mixture is filtered through celite and the solvent removed in vacuo to give 7.51 g. crude oil which crystallizes from ether-pentane to give solid. The solid is "flash chromatographed" on silica gel with 3% acetone in methylene chloride to give the title product of this step, with no trace of isomeric materials by TLC, in this fraction* GC or C¹³ NMR. m.p. 101.5–103.5 $[\alpha]_D^{25}$ +47.14 (CHCl₃) [c=2.07 ].

*A small amount of the isomeric 2β-6α-triphenylmethoxymethyl-tetrahydro-2H-pyranol-5β-ol can then be recovered from the column.

Step F Preparation of 2β-methoxy-4β-(diphenyl t-butylsiloxy) 6α-triphenylmethoxy-methyl-tetrahydro-2H-pyran; a compound C

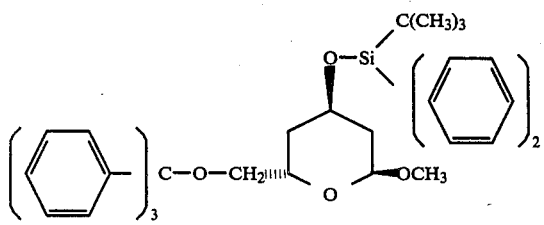

23.25 g (0.05 m) of the alcohol of Step E is dissolved in 207 ml of DMF*, 8.3 g of of imidazole is added followed by 16.74 g of t-butyl diphenyl silyl chloride. When the reaction is complete it is poured into 1 liter of brine and extracted 4 times with 200 ml portions ether. The ether phase is washed three times with 200 ml portions of cold 5% hydrochloric acid, 3 times with 200 ml portions of aqueous sat. sodium bicarbonate, dried over anh. sodium sulfate and evaporated in vacuo to a solid which is recrystallized from ether-hexane to obtain the product of this step as a white cryst. solid m.p. 151°–152° C.

*dimethylformamide

Step G Preparation of 2β-methoxy-4β-(diphenyl t-butylsiloxy)-6α-hydroxymethyl-tetrahydro-2H-pyran; a compound D.

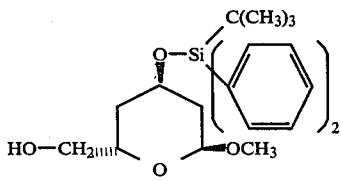

10 g (0.0156 moles) of trityl ether of Step F is dissolved in 300 ml of THF plus 30 ml of t-butyl alcohol. The solution is cooled to −40° C. and 300 ml of ammonia is condensed into the flask. Some cloudiness develops so an additional 170 ml of THF is added. The reaction is maintained at −40° C. while 2.3 g of sodium metal is added over 2 hours. When all the sodium has dissolved, a few chips of ice are added and the dark blue solution becomes colorless. The ammonia is allowed to boil off, the THF phase is filtered and then evaporated to a residue. The residue is taken up in ether, dried over anh. sodium sulfate and evaporated to obtain a residue. The residue is placed on a short column of alumina (Activity III) which is eluted first with toluene to recover the by-product triphenylmethane and then with ethyl acetate to obtain the desired product of this step. $[\alpha]_D^{25} = +63.56$ (CHCl$_3$, c=1.09).

Step H Prepararation of [4β-(diphenyl t-butylsiloxy)-6β-methoxy-tetrahydro-2H-pyran-2-yl]-aldehyde; a compound V.

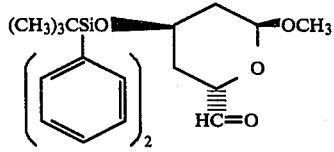

9.596 ml of oxalyl chloride dissolved in methylene chloride is cooled to −50° C. and a solution of 15.61 ml dimethyl sulfoxide (DMSO) dissolved in 50 ml methylene chloride is added at such a rate as to maintain −50° C. The mixture is stirred 2 minutes after addition is complete, followed by the addition of 4.006 g (0.01 moles) of the alcohol of Step F, dissolved in 10 ml methylene chloride over 5 minutes, maintained at −50° C. After 15 min. at −50° the mixture is treated with 69.69 ml of triethylamine in 50 ml methylene chloride and then stirred at −50° C. for 2 hours. Ten mls of brine is added and the cold reaction mixture is poured into 300 ml saturated aqueous sodium bicarbonate. The methylene chloride layer is separated, washed 3 times with aqueous sodium bicarbonate, 2 times with brine, dried over anhydrous sodium sulfate and concentrated to an oil which is chromatographed on silica gel with ether-hexane (1 to 9) to give a yellow oil, which shows carbonyl absorption at 1739 cm$^1$ (IR); $[\alpha]_D^{25} + 51.66$ (CHCl$_3$, c=2.07).

Step I 6α-[2-(2-methyl-1-naphthyl)ethenyl]4β-diphenyl t-butylsiloxy-3,4,5,6-tetrahydro-2β-methoxy-pyran(-trans); a compound IV.

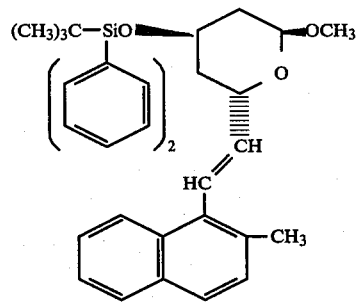

453 mg (0.001 moles) of [1-(2-methylnaphthyl)]-methyltriphenyl-phosphonium iodide is suspended in 50 ml dry benzene cooled to 5° C. and 1.0 ml of a 1.3M solution of butyl lithium in hexane is added dropwise. The resulting red solution is stirred for five minutes before the aldehyde product* of Step H is added in 10 ml benzene. The reaction is warmed to room temperature and stirred overnight. The reaction is briefly heated to reflux until thin layer chromatography indicated complete loss of the aldehyde. One ml of water is added to the resulting tan-colored reaction mixture, the benzene is evaporated, to yield a residue which is taken up in ether, washed with brine, dried over anh. sodium sulfate and evaporated to a tan oil. Chromatography of the oil on silica gel-ether yields a yellow oil—predominately the desired isomeric product of this step (the trans olefin).

*398 mg.

Step J

6α-[2-(2-methyl-1-naphthyl)ethenyl]-3,4,5,6-tetrahydro-4β-(diphenyl t-butylsiloxy)-2H-pyran-2-ol (trans); a compound III.

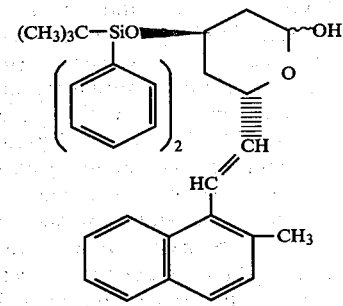

156 mg of the product of Step I is dissolved in 3 ml THF, and 1 ml of 10% aqueous hydrochloric acid is added. The solution is stirred at room temperature for about 18 hours. Solid sodium bicarbonate is added, until a pH of 7 is reached, the THF is evaporated and the residue taken up in methylene chloride. The methylene chloride is washed with brine, dried over anh. sodium sulfate and concentrated to an oil, (106.4 mg) which is the title product of this step, which is then chromatographed on silica gel eluting with methylene chloride-hexane (3/1) to obtain highly refined product (65 mg) for use in Step K, below.

Step K Preparation of 6α-[2-(2-methyl-1-naphtthyl)ethenyl]-3,4,5,6-tetrahydro-4β-diphenyl t-butylsiloxy-2H-pyran-2-one (4R, 6S) (a compound II).

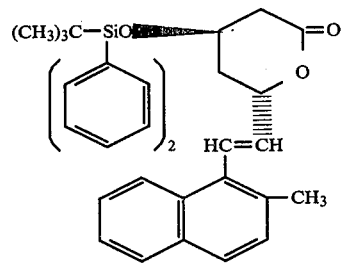

60 mg of the hydroxy product of Step J is dissolved in 10 ml methylene chloride and 180 mg of pyridinium chlorochromate (PCC) added. After stirring for about 18 hours at room temperature, diethyl ether is added, the resulting solid removed by filtration, the organic layer washed with aq. bicarbonate, brine, dried over anh. sodium sulfate and evaporated to 36 mg of a light yellow oil which is the product of this step.

Step L Preparation of 6α-[2-(2-methyl-1-naphthyl)ethenyl]-3,4,5,6-tetrahydro-4β-hydroxy-2H-pryan-2-one (4R, 6S); a compound I.

18 mg of the silyl ether product of Step K, above, is dissolved in 4 ml of dry THF, 5 equivalents of glacial acetic acid are added at room temperature followed by 3 equivalents of tetra-n-butyl ammonium fluoride (as a 1 molar solution in THF). The resulting mixture is stirred (at room temperature) for about 18 hours. The mixture is then concentrated to a small volume and directly chromatographed on silica gel (eluted with 10% ethyl acetate in diethyl ether) to give the title product. NMR of the product shows a multiplet at 5.53δ matching the known compound prepared by the reported method. The absence of any multiplet at 5.05δ indicates the absence of the cis form; thus confirming that the product of this example is essentially in the desired trans form, i.e., the 4R, 6S, isomer.

What is claimed is:

1. An aldehyde compound of the formula:

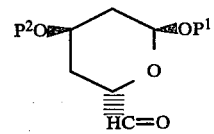

wherein each of $P^1$ and $P^2$, independently, is a protecting group.

2. A compound of claim 1 in which $P^1$ is an unbranched alkyl having from 1 to 4 carbon atoms.

3. A compound of claim 2 in which $P^1$ is methyl.

4. The compound of claim 3 in which $P^2$ is diphenyl t-butylsilyl.

5. A compound of claim 4 which is in the 4R, 6S form.

* * * * *